United States Patent [19]

Zimmer et al.

[11] Patent Number: 5,202,349

[45] Date of Patent: Apr. 13, 1993

[54] SUBSTITUTED PHENYLACETYLENES, PHARMACEUTICAL COMPOSITIONS CONTAINING THESE COMPOUNDS AND PROCESSES FOR THE PREPARATION OF THESE COMPOUNDS AND COMPOSITIONS

[75] Inventors: Oswald Zimmer, Dueren; Werner Vollenberg, Stolberg; Ulrich Seipp, Aachen; Werner Englberger, Stolberg; Michael Haurand, Aachen; Brigitte J. Bosman, Simmerath-Lammersdorf; Johannes Schneider, Stolberg, all of Fed. Rep. of Germany

[73] Assignee: Gruenenthal GmbH, Aachen, Fed. Rep. of Germany

[21] Appl. No.: 732,168

[22] Filed: Jul. 18, 1991

[30] Foreign Application Priority Data

Jul. 26, 1990 [DE] Fed. Rep. of Germany ....... 4023742

[51] Int. Cl.$^5$ .................. A61K 31/38; C07D 307/52
[52] U.S. Cl. .................. 514/438; 546/177; 546/332; 546/336; 549/49; 549/77; 549/441; 514/311; 514/337; 514/443; 514/464; 514/466
[58] Field of Search .................. 549/49, 77, 441; 514/438, 443, 464, 466, 311, 357; 546/332, 336, 177

[56] References Cited

U.S. PATENT DOCUMENTS 4,406,691 9/1983 Szczepanski .................. 71/120

FOREIGN PATENT DOCUMENTS

| 030922 | 6/1981 | European Pat. Off. |
| 196184 | 10/1986 | European Pat. Off. |
| 199985 | 12/1986 | European Pat. Off. |
| 279281 | 8/1988 | European Pat. Off. |
| 292699 | 11/1988 | European Pat. Off. |
| 374602 | 6/1990 | European Pat. Off. |
| 2602767 | 2/1988 | France |
| WO90/12008 | 10/1990 | PCT Int'l Appl. |
| 2196629 | 5/1988 | United Kingdom |

OTHER PUBLICATIONS

Jakschik et al., Biochem. Biophys. Rsh. Comm., 102:624–29 (1981).
Tateson et al., Brit. J. Pharmacol., 94:528–39 (1988).
Summers et al., J. Med. Chem., 31:1960–64 (1988).
Summers et al., J. Med. Chem., 31:3–5 (1988).
Huang et al., J. Med. Chem., 32:1836–42 (1989).
Jackson et al., J. Med. Chem., 31:499–500 (1988).
Summers et al., J. Med. Chem., 30:2121–26 (1987).

Primary Examiner—Richard L. Raymond
Assistant Examiner—Mark W. Russell
Attorney, Agent, or Firm—Foley & Lardner

[57] ABSTRACT

Substituted phenylacetylenes of the formula

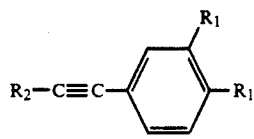

wherein one of the groups $R_1$ is a hydrogen atom and the other represents the group of the formula

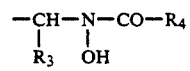

in which $R_3$ is hydrogen, methyl or ethyl and $R_4$ is a methyl or an amino group and wherein $R_2$ represents mono- or binuclear aromatic or heterocyclic residues containing sulfur, nitrogen or oxygen as hetero atoms and optionally being substituted by 1 to 3 substituents as defined, which specifically inhibit 5-lipoxygenase and are useful in pharmaceutical compositions for prophylaxis and treatment of diseases due to the action of leukotrienes.

The compounds may be prepared by reacting a compound of the formula

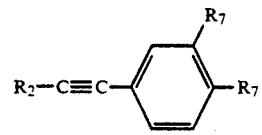

wherein $R_2$ has the same meaning as above and one of the groups $R_7$ is a hydrogen atom and the other represents the group of the formula —$COR_3$, with hydroxylamine to form the oxime which then is reduced to the corresponding hydroxylamine compound into which the group of the formula —$COR_4$ is introduced.

16 Claims, No Drawings

SUBSTITUTED PHENYLACETYLENES, PHARMACEUTICAL COMPOSITIONS CONTAINING THESE COMPOUNDS AND PROCESSES FOR THE PREPARATION OF THESE COMPOUNDS AND COMPOSITIONS

BACKGROUND OF THE INVENTION

Polyunsaturated higher fatty acids such as arachidonic acid in the metabolism of mammals, including man, serve as substrates for the formation of physiologically important eicosanoids such as prostaglandins and leukotrienes (a group of compounds also known as "Slow Reacting Substance of Anaphylaxis" or "SRS-A") The pathway to prostaglandins is catalyzed by cyclo-oxygenase (also named "prostaglandin synthetase") whereas the pathway to leukotrienes is catalyzed by 5-lipoxygenase.

The prostaglandins are products of known beneficial functions in mammals while it is known for the leukotrienes or SRS-A, respectively, that they cause allergic reactions, bronchoconstrictions, inflammations, asthma and numerous other harmful effects Accordingly there is a need for chemically and metabolically stable agents which in the living organism have no effect on the biosynthesis of prostaglandins but inhibit selectively or specifically the activity of 5-lipoxygenase and thus prevent the formation of the undesired leukotrienes.

SUMMARY OF THE INVENTION

It now has been found that certain substituted phenylacetylenes, which are chemically and (when used as therapeutics) metabolically stable compounds, show a specific inhibiting effect on 5-lipoxygenase and are especially suitable for use as antiasthmatics as well as in treatment of anaphylactic shock.

These new substituted phenylacetylenes correspond to the general formula:

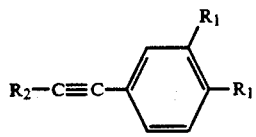

I

In this formula one of the symbols $R_1$ represents a hydrogen atom while the other represents the group of the formula

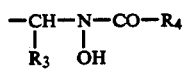

wherein $R_3$ is hydrogen, methyl or ethyl and $R_4$ represents methyl or an amino group.

In formula I $R_2$ represents
a) a mono- or binuclear aromatic radical being a member of the group comprising radicals of the formulae

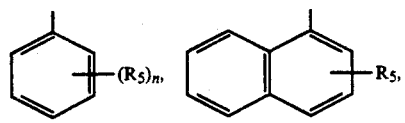

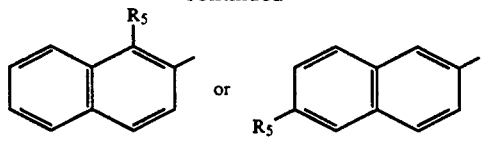

wherein $R_5$ represents hydrogen, a straight chain or branched alkyl, alkoxy or alkylmercapto group containing 1 to 4 carbon atoms, a benzyloxy group, a fluorine or chlorine atom or a trifluoro-methyl group and n represents a number 1, 2, or 3, or
b) a mono- or binuclear heterocyclic radical containing sulfur, nitrogen or oxygen and being a member of the group comprising radicals of the formulae

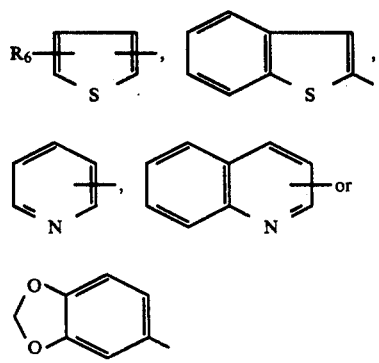

wherein $R_6$ is a hydrogen or a chlorine atom or a methyl group.

Especially in case that $R_3$ is methyl or ethyl the carbon atom bearing $R_3$ becomes an asymmetric center. Such center also results in case $R_5$ represents a 1-methyl propyl group (i.e. a sec.-butyl group). It is to be understood that the present invention includes in such cases the enantiomeres as well as the stereoisomers and—especially in case only one asymmetric center is present—the racemates as well as the optically active forms of the compounds of formula I.

DETAILED DESCRIPTION OF PREFERRED EMBODIMENTS

In preferred compounds of the invention $R_2$ represents one of the groups

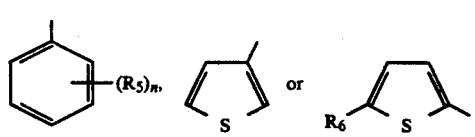

wherein $R_5$, $R_6$ and n have the same meaning as above and $R_5$ preferably represents methoxy.

Out of this group of preferred compounds of the formula I such are especially preferred in which $R_5$ is a methoxy group in 3- and/or 4-position or a fluorine or chlorine atom in 4-position to the acetylene group and wherein n is a number 1 or 2, or such, respectively, in which $R_6$ is hydrogen.

In case $R_2$ represents a pyridine or quinoline group this group preferably in its 3-position is attached to the acetylene moiety.

$R_3$ preferably represents a methyl group.

With respect to the position in which the group $R_1$ is other than hydrogen and is attached to the phenyl ring, the following applies:

In case $R_2$ is a mono- or binuclear optionally substituted aromatic radical as defined above as alternative "a", preferably a phenyl radical bearing 1 to 3 substituents $R_5$, the group $R_1$ preferably is attached to the phenyl ring in 3-position to the acetylene moiety. Such preferred compounds correspond to the formulae

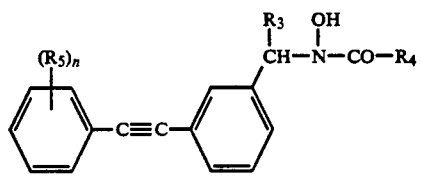

Ia and especially

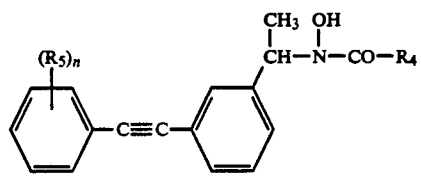

Ib

Preferably in these formulae (especially in formula Ib) $R_4$ represents the amino group:

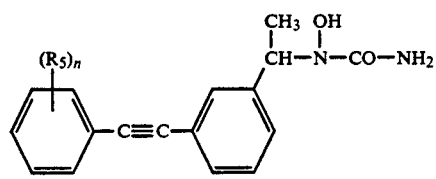

Ic

In these formulae $R_3$, $R_5$ and n have the same meanings as above.

In case, however, $R_2$ represents a thienyl group (optionally substituted by the radical $R_6$), the group $R_1$ preferably is attached to the phenyl ring in 4-position to the acetylene moiety, in which case it furthermore is preferred that $R_4$ represents an amino group. Such preferred compounds correspond to the formula:

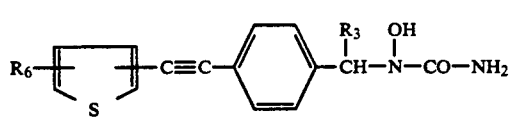

Id wherein $R_3$ and $R_6$ have the same meanings as above.

As stated already hereinabove the compounds of formula I show a specific inhibiting effect on 5-lipoxygenase. This was determined e.g. by in-vitro experiments as follows:

To determine the inhibition of 5-lipoxygenase rat basophilic leukemia cells were cultured in vitro, harvested by centrifugation, washed with 50 mM potassium phosphate buffer of pH 7.4 and then suspended in this buffer at $1.5 \times 10^7$ cells/ml.

To 1 ml each of this suspension there was added indomethacin (10 μM) and calcium chlorid (2 mM) and then the mixture was incubated in presence or absence of a test compound for 3 minutes and thereafter with 20 μM of [$^{14}$C]-arachidonic acid and 20 μM of the calcium ionophore A 23 187 for 10 minutes. The reaction was stopped by adding 20 μl of glacial acetic acid and then the mixture was extracted with ethyl acetate to isolate the metabolites of arachidonic acid formed by the enzymatic action of 5-lipoxygenase. These were separated by thin layer chromatography using a solvent mixture known to be suitable for leukotriene analysis [c.f. Jakschik et al., Biochem. Biophys. Res. Commun. 102, 624 (1981)]. The distribution of the radioactivity to the different metabolites was measured using a TLC Linear Analyzer. By bringing into relationship the percentages of the amount of the products formed under the action of 5-lipoxygenase (5-HETE, isomers of $LTB_4$) in the controls (tests performed in absence of test compounds) and in the presence of test compounds of formula I in different concentrations the "$IC_{50}$-value" (i.e. the concentration of the test compound which causes an 50%-inhibition of the 5-lipoxygenase) is determined. For standardization these values then were brought into relationship to the $IC_{50}$-values determined in the same manner for the standard compound nordihydroguaiaretic acid. These standardized "$IC_{50}$-values (A)" are given in table 1.

The effect of the test compounds on the activity of cyclooxygenase was tested using a suspension of sheep seminal vesicle microsomes in 50 mM potassium phosphate buffer of pH 7.0 which was incubated with the solvent only (as control) or with the test compound and [$^{14}$C]-arachidonic acid. The "$IC_{50}$-values (B)" (i.e. the concentration of the test compound which causes an 50%-inhibition of the cyclooxygenase) were determined by thin layer chromatography and by means of a TLC-Linear-Analyzer.

Thus for instance the following $IC_{50}$ values were determined for the products of the examples listed in table I from which the quotient

TABLE 1

| | $IC_{50}$ [μM] for inhibition of | | |
|---|---|---|---|
| Example | 5-lipoxygenase (A) | cyclooxygenase (B) | Quotient |
| 1 | 0,67 | >500 | >746 |
| 5a | 0,29 | 440 | 1517 |
| 5b | 0,28 | >500 | >1786 |
| 5c | 0,58 | >500 | >862 |
| 7 | 0,65 | >500 | >769 |
| 9 | 0,15 | 100 | 667 |
| 10b | 0,69 | >500 | >725 |
| 10c | 0,27 | >500 | >1852 |
| 10d | 0,55 | 500 | 909 |
| 10g | 0,32 | 270 | 844 |
| 10m | 0,26 | >500 | >1923 |
| 10n | 0,18 | >500 | >2778 |
| 11 | 0,67 | >500 | >746 |
| 15 | 0,41 | 500 | 1220 |
| 16b | 0,29 | 500 | 1724 |
| 16d | 0,37 | 500 | 1351 |
| 16f | 0,41 | 500 | 1220 |

As can be seen from this table the $IC_{50}$-values for the inhibition of cyclooxygenase often are more than 1000 times higher than the $IC_{50}$-values for 5-lipoxygenase inhibition. These results show that the test substances of formula I very specifically only inhibit the activity of 5-lipoxygenase.

The bioavailability of the compounds of formula I after oral administration was characterized by means of an ex vivo biochemical assessment method described by Tateson et al. in Brit. Pharmacol., 94, 528 (1988).

Compounds of formula I were orally administered to male rats (Wistar strain). 1 hour later the rats were bled by heart puncture in letal $CO_2$-narcosis. The 5-lipoxygenase reaction was triggered by the addition of the calcium-ionophor A23187 to an end concentration of 15 pg/ml to aliquots of rat whole blood and subsequent incubation for 30 minutes at 37° C. in a water bath. At the end of the incubation the samples were centrifuged to collect the cell free plasma. The concentration of the immunoreactive LTB$_4$ (iLTB$_4$ ng/ml) in each plasma sample was determined by a LTB$_4$-radioimmunoassay ($^3$H-LTB$_4$-RIA, Amersham) by means of a LTB$_4$-standard curve in diluted rat plasma. For calculation of the percent inhibition of ex vivo iLTB$_4$-formation in whole blood of rats treated with the compounds of formula I rats treated with appropiate vehicle solution were included in all experiments, aliquots of their blood were run in parallel and were processed in the same way as described. The mean iLTB$_4$-formation per ml plasma of these vehicle treated control rats served as 100 percent value of normal control 5-lipoxygenase activity. The percent inhibition of the ex vivo iLTB$_4$-formation after oral administration of compounds of formula I was calculated as follows: 100 minus 100 times the quotient of the mean iLTB$_4$ concentration per ml plasma of the rats treated with compounds of formula I and the mean iLTB$_4$ concentration per ml plasma of the rats treated with compounds of formula I and the mean iLTB$_4$ concentration per ml plasma of the control rats.

Table 2 shows the resulting percent inhibition of the ex vivo iLTB$_4$-formation after oral administration of 21.5 mg/kg of compounds of formula I:

TABLE 2

| Example | % Inhibition | Example | % Inhibition |
|---------|--------------|---------|--------------|
| 2a | 76% | 10d | 99% |
| 5a | 75% | 10e | 81% |
| 5c | 88% | 11 | 76% |
| 5e | 82% | 12 | 87% |
| 7 | 90% | 15 | 77% |
| 8b | 99% | 16b | 91% |
| 10b | 86% | 16f | 97% |

In this assay the product of Example 9 already after oral administration of a dose of 10 mg/kg exerted a 86 % inhibition of the ex vivo iLTB$_4$-formation.

As a test model to evaluate the effects of test compounds in septic shock the endotoxin/galactosamine-induced hepatitis in mice has been used. In this model, the intravenous injection of 0.3 mg/kg endotoxin (lipopolysaccharide from S. abortus equi) in combination with 700 mg/kg galactosamine induces a hepatitis in conscious mice, that is demonstrated 8 hours after the application of endotoxin by an increase of liver specific enzymes (glutamate-pyruvate-transaminase, GPT; sorbitol-dehydrogenase, SDH) in the serum. The intraperitoneal application of 5-lipoxygenase inhibitors 30 minutes before, simultaneously with and 2, 4 and 6 hours after the application of endotoxin inhibitis the hepatitis-induced increase of the serum activities of these enzymes. On administration of compounds of the formula I in doses of 10 mg/kg for each of the five applications the following percentual inhibitions of the increase of the enzymes GPT and SDH were achieved (the increase of enzymatic activities in control animals was set at 100%):

TABLE 3

| Example | Inhibition of increase of | |
|---------|------|------|
|  | GPT | SDH |
| 1 | 47 | 58 |
| 4 | 87 | 81 |

TABLE 3-continued

| Example | Inhibition of increase of | |
|---------|------|------|
|  | GPT | SDH |
| 9 | 94 | 90 |

The antiasthmatic activity of compounds of formula I was tested in narcotised and ventilated guinea pigs. For the induction of an asthmatic reaction, the animals were passively sensitized by a single intraperitoneal injection of anti-ovalbumin serum. 48 hours afterwards the asthmatic reaction was elicited by intravenous challenge with 0.2 mg/kg ovalbumin. The immediately resulting bronchoconstriction was measured as increase in overflow according to the Konzett-Rbssler method for a period of 10 minutes. Effects caused by histamine, serotonin and sympathic counterreaction were eliminated by intravenous pretreatment with 2.15 mg/kg mepyramine, 46.4 μg/kg propranolol, 4.64 mg/kg atropin and 1 mg/kg methysergide, all given 5 minutes before challenge.

After oral administration of the product of Example 5a or of the product of Example 9, in doses of 100 mg/kg each, the bronchoconstriction was inhibited by 54% or by 67%, respectively.

Due to their favorable effect on the metabolism of polyunsaturated fatty acids, particularly their selective inhibitory action on the 5-lipoxygenase induced production of metabolites of arachidonic acid such as 5-hydroxyperoxyeicosatetraenoic acid (5-HPETE), 5-hydroxyeicosatetraenoic acid (5-HETE) or SRS-A, respectively, the new compounds of formula I exhibit various physiologically valuable actions such as antianaphylactic, antiasthmatic, antiallergic, antiphlogistic, blood pressure lowering and cerebral- and coronary-circulation improving effects, decreasing the risc of leukocyte aggregation and preventing the formation of leukocyte thrombi and other actions. Due to their chemical and metabolic stability in therapeutical application the compounds of formula I according to the invention are storable and suitable for use as medicaments such as antianaphylactics, antiasthmatics, antiallergics, antiphlogistics, antihypertensive agents, antithrombotic agents, agents for use in treatment or prophylaxis of ischemic myocardial infarction, disorders of coronary and/or cerebral arteries and others.

The compounds of formula I have a low degree of toxicity which is observed only at far higher doses than those to be administered for therapeutic or prophylactic purposes. Accordingly these compounds can be administered to human and animal patients, preferably in form of suitable pharmaceutical compositions.

Further objects of the invention accordingly include medicaments containing one or more of the substituted phenylacetylenes according to the invention. The dosage of the active component to be administered to a patient depends, for instance, on the patients body weight, on the administration route and form, on the indication and on the state of disease in the individual patient to be treated. In consideration of these factors in general a unit dosage form of a medicament according to the present invention contains about 0.01 to 50 mg of the active ingredient, whereby compositions for parenteral administration preferably contain about 0.01 to 10 mg and those for oral or rectal administration preferably contain about 0.1 to 50 mg per unit dose.

The medicaments for parenteral application may be solutions or suspensions but may also be dry formulations suitable for easy reconstitution.

Spray forms are very useful application forms for intranasal or oral applications of the compounds of formula I or for the administration of these substances to the bronchia.

Compositions for oral administration such as tablets, dragees, capsules, granules, drops and syrups are very suitable for prophylactic or therapeutic administration of the compounds of formula I in several cases. Other compositions such as suppositories or compositions for percutaneous application of the compounds of formula I, such as plasters or the like containing a solution of the active ingredient and optionally a known membrane penetration enhancer (such as an N-alkyl lactam) are also very convenient in many cases.

The pharmaceutical compositions described above for peroral, rectal, percutaneous or intramuscular administration of the compounds of formula I preferably may be such from which at least a portion of the active ingredient has a delayed release. Thus for a longer period of time, for instance 24 hours, a steady supply of the active ingredient to the patient can be achieved.

All of the general types of pharmaceutical compositions to which the invention is applicable and their preparation in principle are known per se and as the compounds of formula I are chemically stable products their incorporation into such pharmaceutical compositions in the form and dosage desired poses no problems or difficulties for an ordinarily skilled pharmacist. In the production of pharmaceutical compositions according to the invention conventionally used inorganic or organic adjuvants such as diluents, carriers, binders, lubricants, colors, flavorings etc. are formulated together with the active ingredient of formula I in accordance with accepted standards in a manner known per se. It should be mentioned that the compositions for parenteral use must be sterile and, if prepared in liquid form, isotonic.

The process for the manufacture of the compounds of formula I according to the invention comprises
i) reacting a compound of the formula

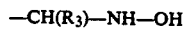

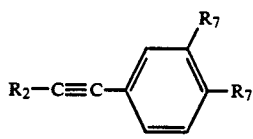 II wherein $R_2$ has the same meaning as above and in which one of the symbols $R_7$ represents a hydrogen atom while the other represents the group —$COR_3$ in which $R_3$ is as defined above,
with hydroxylamine or with a salt thereof to form the oxime which then is reduced to a compound of the formula

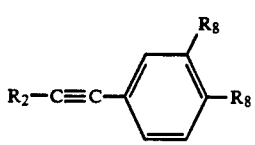 III wherein $R_2$ has the same meaning as above and in which one of the symbols $R_8$ represents a hydrogen atom while the other represents the group of the formula

—CH($R_3$)—NH—OH

This reaction is performed in a manner known per se for instance in alcoholic or aqueous-alcoholic solution in presence of suitable bases such as e.g. pyridine, potassium carbonate or sodium acetate and the like at temperatures of about 20° C. to 60° C.

The reduction is performed by means of boron hydrides, preferably sodium cyanoborohydride, in presence of acids such as acetic acid or ethanolic hydrochloric acid at temperatures of e.g. 20° C. to 60° C. or in alcoholic solution with boraneamine complexes, such as e.g. the borane-pyridine complex, or with the borane-tetrahydrofuran complex in presence of an acid, e.g. 6 n hydrochloric acid at temperatures from about 20° C. up to about 20° C. (c.f. J. B. Summers et al., J. Med. Chem. 31 1960 (1988).

The hydroxylamine derivative of formula III is transformed into the corresponding compound of formula I by introducing the acyl group of the formula —$COR_4$.

To prepare compounds of formula I in which $R_4$ represents the amino group ($NH_2$; N-hydroxy ureas) the compound of formula III is reacted with trimethylsilyl isocyanate in presence of inert solvents, preferably cyclic ethers such as tetrahydrofuran or 1,4-dioxane, while heating to temperatures between about 20° C. and the boiling temperature of the solvent. The resulting intermediate then is hydrolyzed to eliminate the trimethylsilyl group, e.g. by treatment with a saturated aqueous solution of ammonium or sodium chloride to obtain the desired compound of formula I in which $R_4$ is $NH_2$.

Alternatively such a compound of formula I in which $R_4=NH_2$ may also be obtained by reacting a compound of formula III either with sodium or potassium cyanate in an acidic solution or with phosgene or a lower alkyl or benzyl chloroformate in presence of an agent capable of binding acids, such as sodium or potassium carbonate, followed by a treatment with ammonia or e.g. ammonium carbonate.

To prepare compounds of formula I in which $R_4$ represents the methyl group (acetohydroxamic acids) the compound of formula III, optionally without isolation from the reaction mixture in which it was prepared, is reacted with an acetylating agent, preferably with acetic anhydride or acetyl chloride, in presence of an agent capable of binding acids, such as pyridine or quinoline, whereby a compound of formula

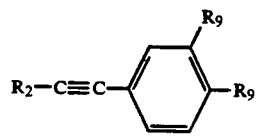 IV wherein one of the symbols $R_9$ represents a hydrogen atom whereas the other represents the group of the formula

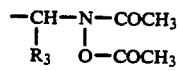

is formed. On selective hydrolysis in the presence of an alcoholic solvent such as methanol or ethanol containing a base at temperatures of about 20° C. to 60° C., the 0-acetyl group is split off and the desired compound of formula I in which $R_4$ is methyl is obtained. Suitable bases for this hydrolysis include e.g. 0.1 n to 1 n potassium, sodium or lithium hydroxide which optionally may be added in form of aqueous solutions to the alcoholic solution of the compound of formula IV.

ii) The compounds of formula I may furthermore be prepared by reacting a compound of the formula

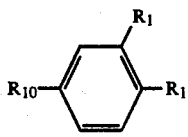

V wherein $R_1$ has the same meaning as above and $R_{10}$ represents a bromine or iodine atom with a compound of the formula

VI wherein $R_2$ is as defined above in the presence of a secondary or tertiary amine, which is liquid in the temperature range of about 0° C. to 80° C., especially a dialkyl or trialkyl amine containing 2 or 3 carbon atoms in each alkyl group or pyrrolidine or piperidine, and in the presence of catalytic amounts of a complex palladium catalyst, such as bis-(triphenylphosphine)-palladium-(II) chloride or acetate or tetrakis-(triphenylphosphine)palladium and optionally catalytic amounts of copper(I)iodide at about 20° C. to 80° C. The term "catalytic amount" means an amount of about 0.01 to 5 percent per mole of the compound of formula VI used.

The starting materials of formulae II or V, respectively, are obtained-in a manner known per se.

For instance the compounds of formula II may be obtained in a high yield by reacting
a compound of formula VI with a compound of the formula

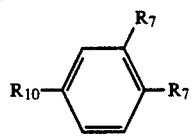

VII wherein $R_7$ and $R_{10}$ have the same meanings as above or
a compound of the formula

VIII with a compound of the formula

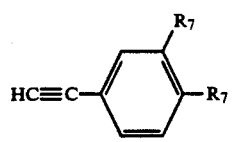

IX wherein $R_2$, $R_7$ and $R_{10}$ have the same meanings as above under the conditions described above for the reaction of a compound of formula V with a compound of formula VI.

To prepare a starting compound of formula V a compound of formula VII may be reacted with hydroxylamine or a salt thereof followed by reduction of the resulting oxime to the corresponding hydroxylamine derivative and finally introducing the group —$COR_4$ in a manner analogous to that described above (in i) for the preparation of a compound of formula I starting with a compound of formula II.

The following non-limiting examples serve further to illustrate the invention, especially the processes for the prepation of the compounds of formula I, the starting materials and the intermediates used in these processes. No importance was attached to obtain maximum yields.

All temperature references are uncorrected

The $^1$H-nuclear magnetic spectra were measured at 300 MHz. The chemical shifts are reported in ppm.

The term "ether" as used in the examples means diethyl ether and the term "petroleum ether" indicates that fraction having a boiling range of 50° C. to 70° C. unless otherwise mentioned.

In column chromatography, silica gel ("Kieselgel 60, 0.040–0.063 mm of E. Merck AG, Darmstadt, Germany) was used as the stationary phase unless otherwise indicated.

The reactions in most instances were monitored by thin layer chromatography on plates precoated with silica gel ("HPTLC Fertigplatten, Kieselgel 60 F 254" of E. Merck AG, Germany). In these cases the solvents used are indicated in the examples by "(TLC: ... )".

The ratio of the components of the solvent mixtures used in all of the chromatographic procedures is given in volume/volume.

- EXAMPLE 1

N-[3-(Naphth-2-yl-ethynyl)-benzyl]-acetohydroxamic acid a) 3-(Naphth-2-yl-ethynyl)-benzaldehyde To a solution of 15.3 g of naphth-2-yl-acetylene and 16.65 g of -bromobenzaldehyde in 120 ml of absolute triethylamine were added at a bath temperature of 50° C. while stirring in an atmosphere of dry nitrogen 1.05 g of bis-(triphenylphosphine)-palladium(II) chloride and 0.07 g of copper(I) iodide. Then the mixture was stirred at a bath temperature of 70°-80° C. (TLC: petroleum ether/ether-5:1). When the reaction was finished the mixture was filtered, the residue washed with ethyl acetate and then the filtrates were evaporated in a vacuum. By column chromatography with petroleum ether/ether (4:1) the residue is purified to yield 15.1 g (65.5% of the theoretical yield) of the title compound in the form of crystals melting at 90°-92° C.

$^1$H-NMR (CDCl$_3$) 7.50–7.61 (m, 4H, aromat.); 7.81–7.88 (m, 5H, aromat.); 8.08 (s, 2H, aromat.); 10.02 (s, 1H, CHO)

b) 3-(Naphth-2-yl-ethynyl)-benzaldehyde oxime

To a solution of 15 g of the product obtained in Example 1a in 80 ml of methanol was added a solution of 6.08 g of hydroxylamine hydrochloride and of 5.63 g of sodium acetate in 80 ml of water. The mixture was stirred at a bath temperature of 60° C. (TLC: petroleum ether/ether—4:1). When the reaction was complete the methanol was evaporated and the aqueous residue extracted twice with ethyl acetate. The extracts were washed with water, then with saturated sodium chloride solution. After drying and evaporating in a vacuum 15.4 g (97.2% of the theoretical yield) of the title compound were obtained in form of a sand-colored powder (mixture of isomers). E-isomer:

$^1$H-NMR (CDCl$_3$): 7.34–7.43 (m, 1H, aromat.); 7.51–7,61 (m, 5H, aromat.); 7.78–7.86 (m, 4H, aromat.); 8.07 (s, 1H, aromat.); 8.12 (s, 1H, N=CH)

c) N-[3-(Naphth-2-yl-ethynyl)-benzyl]-acetohydroxamic acid

To a solution of 15.3 g of the product obtained in Example 1b in 170 ml of glacial acetic acid were added while stirring at a bath temperature of 50°–55° C. in an atmosphere of dry nitrogen in small portions 4.45 g of sodium cyanoborohydride. After stirring for an additional hour the mixture was allowed to cool and, after adding 13.4 ml of acetic anhydride stirred for further 12 hours. Then the mixture was evaporated in a vacuum, the residue diluted with water and extracted three times with ethyl acetate. The extracts were washed twice each with saturated solutions of sodium hydrogen carbonate and of sodium chloride, and then dried over sodium sulfate. By chromatography with petroleum ether/ether (1:1) of the residue obtained on evaporation the O,N-diacetylated intermediate (a compound of the general formula IV) was isolated which then was dissolved in 100 ml of methanol. After adding 10 ml of a 10% aqueous solution of sodium carbonate the mixture was heated, while stirring, for two hours in a bath at 60° C. The residue obtained on evaporation in a vacuum was recrystallized from ethyl acetate/hexane to yield 11.14 g (62,6% of the theoretical yield) of the title compound in the form of colorless crystals melting at 144°–146° C.

$^1$ H-NMR (DMSO-d$_6$): 2.21 (s, 3H, NCOCH$_3$); 4.81 (s, 2H, NCH$_2$);
7.34–7.36 (m, 2H, aromat.): 7.50–7.58
(m, 5H, aromat.); 7.81–7.84 (m, 3H, aromat.);
8.05 (s, 1H, aromat.)

EXAMPLE 2

Proceeding as described in Examples 1a–1c but using the appropriate reactants there were obtained:

N-{1-[4-(Phenylethynyl)-phenyl]-ethyl}-acetohydroxamic acid

Melting point: 137°–138° C.
$^1$H-NMR (DMSO-D$_6$): 1.45, 1.48 (d, 3H, NCCH$_3$); 2.03 (s, 3H, NCOCH );
5.58–5.72 (m, 1H, NCH); 7.32–7.58
(m, 9H, aromat.)

b) N-[3-(Naphth-1-yl-ethynyl)-benzyl]-acetohydroxamic acid

Melting point: 98°–100° C.
$^1$H-NMR (DMSO-d6): 2.08 (s, 3H, NCOCH ); 4.75 (s, 2H., NCH2);
7.32–7.74 (m, 7H, aromat.);
7.83, 7.85 (d, 1H, aromat.); 7.95–8.05
(m, 2H, aromat.); 8.35, 8.38 (d, 1H, aromat.)

c) N-{1-[3-(4-Trifluoromethyl-phenylethynyl)-phenyl]-ethyl}-acetohydroxamic acid Melting point:-97°–98° C.
$^1$H-NMR (DMSO-d6): 1.47, 1.49 (d, 3H, NCCH ); 2.03 (s, 3H, NCOCH );
5.58–5.69 (m, 1H, NCH); 7.40–7.53
(m, 4H, aromat.); 7.78 (s, 4H, aromat.)

d) N-{1-[3-(2,4,6-Trimethyl-phenylethynyl)-phenyl]-ethyl}-acetohydroxamic acid Melting point: 45°–47° C.
$^1$H-NMR (DMSO-d ): 1.46, 1.49 (d, 3H, NCCH ); 2.03 (s, 3H, NCOCH );
2.27 (s, 3H, CH$_3$); 2.42 (s, 6H, CH$_3$);
5.57–5.68 (m, 1H, NCH); 6.95 (s, 2H, aromat.);
7.32–7.45 (m, 4H, aromat.)

EXAMPLE 3

N-[3-(-Phenylethynyl)-benzyl]-acetohydroxamic acid a) 3-(Phenylethynyl)-benzaldehyde oxime

The procedure was the same as described in Example 1b, except there were used 16.5 g of 3-(phenylethynyl)-benzaldehyde, 8.3 g of hydroxylamine hydrochloride and 8.2 g of sodium acetate to give 16.8 g (94.8% of the theoretical yield) of the title compound in form of a yellowish powder (mixture of isomers).

b) N-[3-(Phenylethynyl)-benzyl]-acetohydroxamic acid

Following the procedure described in Example 1c 11.95 g of the product obtained in Example 3a were reduced with 5.09 g of sodium cyanoborohydride and the reaction mixture then was treated with 12.8 ml of acetic anhydride. The intermediate thus obtained was reacted as described in Example 1c to yield 9.48 g (66.2% of the theoretical yield) of colorless crystals of the title compound melting at 91°–93° C.

$^1$H-NMR (DMSO-d$_6$): 2.08 (s, 3H, NCOCH$_3$); 4.72 (s, 2H, NCH$_2$);
7.30–7.37 (m, 1H, aromat.); 7.40–7.48
(m, 6H, aromat.); 7.54–7.58 (m, 2H, aromat.)

c) The product obtained in Example 3b may also be prepared as follows:

i) 3-Bromobenzyl-acetohydroxamic acid 4.0 g of 3-bromobenzaldehyde oxime are reacted following the procedure described in Example 1c with 1.8 g of sodium cyanoborohydride and thereafter with 3.8 ml of acetic anhydride. The intermediate thus obtained is treated with aqueous sodium carbonate solution to yield the title compound (3.32 g =67.9% of the theoretical yield) as an almost colorless powder melting at 63°–64° C.

$^1$H-NMR (CDCl$_3$): 2.18 (s, 3H, NCOCH$_3$); 4.78 (s, 2H, NCH$_2$);
7.20–7.50 (m, 4H, aromat.)

ii) N-[3-(Phenylethynyl)-benzyl]-acetohydroxamic acid

Following the procedure described in Example 1a 2.2 g of the product obtained in Example 3c)i) were reacted with 1.65 ml of phenylacetylene in 30 ml of absolute triethylamine in presence of 0.21 g of bis-(triphenylphosphine)palladium(II) chloride and 0.02 g of copper(I) iodide. The crude product was purified by HPLC with methanol/water (4:1), followed by recrystallization from ethyl acetate/n-hexane to yield 0.98 g (41.2% of the theoretical yield) of the title compound the physical and spectroscopic data of which are identical to those of the product obtained according to Example 3b.

EXAMPLE 4

N-[3-(4-Methoxy-phenylethynyl)-benzyl]-acetohydroxamic acid a) 3-(4-Methoxy-phenylethynyl)-benzaldehyde 4-Methoxyphenylacetylene was reacted with 3-bromobenzaldehyde in the manner described in Example 1a to yield the title compound in form of white crystals melting at 52°–53° C.

$^1$H-NMR (CDCl$_3$): 3.84 (s, 3H, OCH$_3$); 6.88–6.91 (m, 2H, aromat.);
  7.44–7.53 (m, 3H, aromat.): 7.73–7.76
  (m, 1H, aromat.); 7.80–7.83 (m, 1H, aromat.);
  8.00–8.02 (m, 1H, aromat.); 10.02 (s, 1H, CHO)

b) 3-(4-Methoxy-phenylethynyl)-benzaldehyde oxime

The procedure was the same as described in Example 1b, except there were used a solution of the product obtained in Example 4a in ethanol and pyridine (instead of sodium acetate as base) and then hydroxylamine hydrochloride was added. The crude product was purified by chromatography with petroleum ether/ethyl acetate (3:1) to yield 10.67 g (93.8% of the theoretical yield) of the title compound Light yellow crystals melting at 90°–91° C.

$^1$H-NMR (CDCl$_3$): 3.83 (s, 3H, OCH$_3$); 6.87 <- 6.90 (m, 2H, aromat.);
  7.33–7.38 (m, 1H; aromat.); 7.45–7.55
  (m, 4H, aromat.); 7.70, 7.71 (d, 1H, aromat.);
  8.12 (s, 1H, N=CH)

c) N-Acetoxy-N-[3-(4-methoxy-phenylethynyl)-benzyl]-acetamide

Following the procedure described in Example 1c 10.23 g of the product obtained in Example 4b were dissolved in 120 ml of glacial acetic acid and reacted with 3.84 g of sodium cyanoborohydride, thereafter with 8.8 ml of acetic anhydride. The crude product was purified by chromatography with ethyl acetate/petroleum ether (1:1) to yield 9.98 g (72.2% of the theoretical yield) of the title compound in form of a colorless oil.

$^1$H-NMR (CDCl$_3$): 2.13 (s, 3H, NCOCH$_3$); 2.20 (s, 3H, NOCOCH$_3$);
  3.82 (s, 3H, OCH$_3$); 4.86 (s, 2H, NCH$_2$);
  6.85–6.90 (m, 2H, aromat.); 7.22–7.34
  (m, 2H, aromat.); 7.42–7.49 (m, 4H, aromat.)

d) N-[3-(4-Methoxy-phenylethynyl)-benzyl]-acetohydroxamic acid

To a solution of 1.0 g of the product obtained in Example 4c in 10 ml of methanol 0.205 g of anhydrous potassium carbonate were added while stirring at room temperature. When the reaction was finished (TLC: ethyl acetate/petroleum ether—1:1) the mixture was acidified by adding 5% hydrochloric acid and diluted with ethyl acetate. The organic layer was separated, washed with water and evaporated in a vacuum. The remaining oil solidified to white crystals on drying over phosphorus pentoxide in an exsiccator. Thus 0.853 g (97.6% of the theoretical yield) of the title compound melting at 124°–126° C. were obtained.

$^1$H-NMR (CDCl$_3$): 2.17 (s, 3H, NCOCH$_3$); 3.82 (s, 3H, OCH$_3$);
  4.79 (s, 2H, NCH ); 6.86–6.89 (m, 2H, aromat.);
  7.24–7.55 (m, 6H, aromat.)

EXAMPLE 5

By using the appropriate reactants and otherwise proceeding as described in Examples 4a–4d there were obtained:

a)
N-{1-[3-(4-Methoxy-phenylethynyl]-phenyl}-ethyl-acetohydroxyamic acid

Colorless viscous oil
$^1$H-NMR (DMSO-d$_6$): 1.46, 1.48 (d, 3H, NCCH$_3$); 2.03 (s, 3H, NCOCH$_3$);
  3.79 (s, 3H, OCH$_3$); 5.61–5.63 (m, 1H, NCH);
  6.95–6.99 (m, 2H, aromat.); 7.32–7.52
  (m, 6H, aromat.)

b)
N-{1-[3-(3,4-Dimethoxy-phenylethynyl)-phenyl]-ethyl}-acetohydroxamic acid

Melting point: 107°–108° C.
$^1$H-NMR (DMSO-d$_6$): 1.45, 1.48 (d, 3H, NCCH$_3$); 2.02 (s, 3H, NCOCH$_3$);
  3.79 (s, 3H, OCH$_3$); 3.80 (s, 3H, OCH$_3$);
  5.53–5.69 (m, 1H, NCH); 6.96–6.99
  (m, 1H, aromat.); 7.10–7.14 (m, 2H, aromat.);
  7.31–7.45 (m, 4H, aromat.)

c)
N-{1-[3-(3-Methoxy-phenylethynyl)-phenyl]-ethyl}-acetohydroxamic acid

Colorless viscous oil
$^1$H-NMR (CDCl ): 1.53–1.56 (d, 3H, NCCH$_3$); 2.15 (s, 3H, NCOCH$_3$);
  3.82 (s, 3H, OCH$_3$); 4.99–5.18 and 5.78–5.89
  (m, 1H, NCH); 6.88–6.92 (m, 1H, aromat.);
  7.05–7.14 (m, 2H, aromat.); 7.23–7.54
  (m, 5H, aromat.)

d)
N-{1-[4-(3,4-Dimethoxy-phenylethynyl)-phenyl]-ethyl}-acetohydroxamic acid

Melting point: 123°–124° C.
$^1$H-NMR (DMSO-d$_6$): 1.45, 1.47 (d, 3H, NCCH$_3$); 2.03 (s, 3H, NCOCH$_3$);
  3.79 (s, 3H, OCH$_3$); 3.80 (s, 3H, OCH$_3$);
  5.62–5.64 (m, 1H, NCH); 6.95–6.98
  (m, 1H, aromat.); 7.07–7.12 (m, 2H, aromat.);
  7.32–7.35 (m, 2H, aromat.); 7.45–7.48
  (m, 2H, aromat.)

e)
N-[3-(4-Isopropyl-phenylethynyl)-benzyl]-acetohydroxamic acid

Melting point: 120°–122° C.
1H-NMR (DMSO-d$_6$): 1.20–1.23 (d, 6H, C(CH$_3$)2); 2.07
  (s, 3H, NCOCH$_3$); 2.87–2.96 (m, 1H, CH(C)$_2$);
  4.70 (s, 2H, NCH$_2$); 7.26–7.48
  (m, 8H, aromat.)

f)
N-{1-[3-(4-Isopropyl-phenylethynyl)-phenyl]-ethyl}-acetohydroxamic acid

Colorless viscous oil
$^1$H-NMR (DMSO-d$_6$): 1.20, 1.22 (d, 6H, C(CH$_3$)$_2$); 1.46, 1.48
  (d, 3H, NCCH$_3$); 2.02 (s,.3H, NCOCH$_3$);

2.87–2.97 (m, 1H, CH(C)$_2$); 5.55–5.69
(m, 1H, NCH); 7.27–7.49 (m, 8H, aromat.)

g)
N-{1-[3-(4-Methoxy-naphth-1-yl-ethynyl)-phenyl]-ethyl}-acetohydroxamic acid

Melting range: 70°–75° C.
$^1$H-NMR (DMSO-d$_6$): 1.51, 1.53 (d, 3H, NCCH$_3$); 2.07 (s, 3H, NCOCH$_3$):
4.03 (s, 3H, OCH$_3$); 5.63–5.76 (m, 1H, NCH);
7.01, 7.04 (d, 1H, aromat.); 7.38–7.45
(m, 2H, aromat.); 7.55–7.80 (m, 5H, aromat.);
8.23–8.35 (m, 2H, aromat.)

N-{1-[4-(4-Methoxy-naphth-1-yl-ethynyl)-phenyl]-ethyl}-aceto-hydroxamic acid

Melting point: 139°–142° C.
$^1$H-NMR (DMSO-d$_6$): 1.47, 1.49 (d, 3H, NCCH$_3$); 2.03 (s, 3H, NCOCH$_3$);
4.03 (s, 3H, OCH$_3$); 5.59–5.72 (m, 1H, NCH);
7.01, 7.04 (d, 1H, aromat.); 7.37–7.40
(m, 2H, aromat.); 7.59–7.77 (m, 5H, aromat.);
8.21, 8.24 (d, 1H, aromat.); 8.29, 8.30
(d, 1H, aromat.)

i)
N-{1-[3-(2-Methoxy-phenylethynyl)-phenyl]-ethyl}-acetohydroxamic acid viscous material 1H-NMR (DMSO-d$_6$): 1.46, 1.48 (d, 3H, NCCH$_3$); 2.03 (s, 3H, NCOCH$_3$);
3.86 (s, 3H, OCH$_3$); 5.57–5.70 (m, 1H, NCH);
6.94–6.99 (m, 1H, aromat.); 7.06–7.08 k)
N-{1-[3-(2-Methoxy-napth-1-yl-ethynyl)-phenyl]-ethyl}-acetohydroxamic acid

Melting point: 138°–140° C.
$^1$H-NMR (DMSO-d$_6$) 1.49, 1.51 (d, 3H, NCCH$_3$); 2.04 (s, 3H, NCOCH$_3$);
4.02 (s, 3H, OCH$_3$); 5.65–5.67 (m, 1H, NCH);
7.37–7.64 (m, 7H, aromat.); 7.91, 7.94
(d, 1H, aromat.); 8.00, 8.03 (d, 1H, aromat.);

l) N-{1-[3-(3,4,5-Trimethoxy-phenylethynyl)-phenyl]-ethyl}-acetohydroxamic acid

Melting point: 145° C.
$^1$H-NMR (DMSO-d$_6$): 1.46, 1.48 (d, 3H, NCCH$_3$); 2.03 (s, 3H, NCOCH$_3$);
3.70 (s, 3H, OCH$_3$); 3.82 (s, 6H, OCH$_3$);
5.58–5.63 (m, 1H, NCH); 6.85 (s, 2H, aromat.);
7.35–7.47 (m, 4H, aromat.)

m)
N-{1-[3--(4-Methylphenylethynyl)-phenyl]-ethyl}-acetohydroxamic acid viscous material $^1$H-NMR (DMSO-d$_6$): 1.45, 1.48 (d, 3H, NCCH$_3$); 2.02 (s, 3H,NCOCH$_3$);
2.34 (s, 3H, CH$_3$); 5.61–5.63 (m, 1H, NCH);
7.22–7.25 (m, 2H, aromat.); 7.33–7.46
(m, 6H, aromat.)

n)
N-[3-(2-Methoxy-phenylethynyl)-benzyl-]-acetohydroxamic acid viscous oil $^1$H-NMR (DMSO-d$_6$): 2.19 (s, 3H, NCOCH$_3$); 3.98 (s, 3H, OCH$_3$);
4.83 (s, 2H, NCH$_2$); 7.08–7.13
(t, 1H, aromat.); 7.20, 7.23 (d, 1H, aromat.);
7.41–7.63 (m, 6H, aromat.)

o)
N-[3-(4-Chlorophenylethynyl)-benzyl]-acetohydroxamic acid

Melting point: 149° C.
$^1$H-NMR (DMSO-d$_6$): 2.06 (s, 3H, NCOCH$_3$); 4.70 (s, 2H, NCH$_2$);
7.31–7.60 (m, 8H, aromat.)

EXAMPLE 6

N-Hydroxy-N-[3-(naphth-2-yl-ethynyl)-benzyl]-urea 2.07 g of the product obtained in Example 1b were dissolved in 20 ml of glacial acetic acid and reduced to the corresponding hydroxylamine by reacting with 0.60 g of sodiumcyanoborohydride in the manner described in Example 1c. To a solution of this reduction product in 25 ml of absolute dioxane 2.1 ml of trimethylsilylisocyanate were added and then the mixture was boiled for three hours under reflux. After cooling 50 ml of ethyl acetate were added followed by saturated ammonium chloride solution. The organic layer was separated, washed with saturated ammonium chloride solution and twice with saturated sodium chloride solution, dried over sodium sulfate and evaporated in a vacuum. The oily residue was purified by chromatography with ethyl acetate/petroleum ether (25:1) followed by recrystallization of the product from ethyl acetate/n-hexane. Thus 1.45 g (61.0% of the theoretical yield) of the title compound were obtained in form of colorless crystals melting at 184–186° C.

$^1$H-NMR (DMSO-d$_6$): 4.57 (s, 2H, NCH$_2$); 6.44 (s, 2H, NH$_2$);
7.32–7.44 (m, 2H, aromat.); 7.48–7.65
(m, 5H, aromat.); 7.95–7.99 (m, 3H, aromat.);
8.21 (s, 1H, aromat.)

EXAMPLE 7

N-Hydroxy-N-[-3-(naphth-1-yl-ethynyl)-benzyl]-urea 5.43 g of 3-(naphth-1-yl-ethynyl)-benzaldehyde oxime were reduced in the manner described in Example 1c with 1.96 g of sodium cyanoborohydride. To a solution of the hydroxylamine compound thus obtained in 60 ml of absolute tetrahydrofuran 4 ml of trimethylsilylisocyanate were added and then the mixture was stirred for 4 hours at a bath temperature of 50° C. After working up and purifying in the manner described in Example 6 3.78 g (59.7% of the theoretical yield) of the title compound were obtained which formed colorless crystals melting at 170°–172° C.

$^1$H-NMR (DMSO-d$_6$): 4.59 (s, 2H, NCH$_2$); 6.44 (s, 2H, NH$_2$);
7.35–7.46 (m, 2H, aromat.); 7.55–7.73
(m, 5H, aromat.); 7.80–7.84 (m, 1H, aromat.);
(m, 1H, aromat.)

EXAMPLE 8

By using the appropriate reactants and otherwise proceeding as described in Examples 1 and 7 there were obtained:

a)
N-Hydroxy-N-{1-[3-(4-methoxy-naphth-1-yl-ethynyl)-phenyl]-ethyl}-urea

Melting point: 162°–164° C.
$^1$H-NMR (DMSO-d$_6$): 1.45, 1.47 (d, 3H, NCCH$_3$);
4.03 (s, 3H, OCH$_3$);

5.29–5.40 (m, 1H, NCH); 6.37 (s, 2H, NH₂);
7.02, 7.05 (d, 1H, aromat.); 7.38–7.40
(m, 2H, aromat.); 7.50–7.80 (m, 5H, aromat.);
8.22–8.33 (m, 2H, aromat.)

b)
N-Hydroxy-N-{1-[3-(4-fluorophenylethynyl)-phenyl]-ethyl}-urea

Melting point: 143°–144° C.
$^1$H-NMR (DMSO-d₆): 1.42, 1.44 (d, 3H, NCCH₃);
5.26–5.36
(m, 1H, NCH); 7.22–7.28 (m, 2H, aromat.);
7.32–7.43 (m, 3H, aromat.); 7.51
(s, 1H, aromat.); 7.59–7.64 (m, 2H, aromat.)

c)
N-Hydroxy-N-{1-[3-(3,4-methylendioxy-phenylethynyl)-phenyl]-ethyl}-urea

Melting point: 153°–155° C.
$^1$H-NMR (DMSO-d₆): 1,42, 1,44 (d, 3H, NCCH₃);
5.26–5.35
(m, 1H, NCH); 6.08 (s, 2H, OCH₂O);
6.34 (s, 2H, NH₂); 6.93–6.96 (m, 1H, aromat.);
7.06–7.10 (m, 2H, aromat.); 7.30–7.39
(m, 3H, aromat.); 7.48 (s, 1H, aromat.)

d)
N-Hydroxy-N-{1-[3-(4-tert-butyl-phenylethynyl)-phenyl]-ethyl}-urea

Melting point 74°–76° C.
$^1$H-NMR (DMSO-d₆): 1,30 (s, 9H, t.-C₄H₉); 1.43, 1.45 (d, 3H, NCCH₃);
5.28–5.36 (m, 1H, NCH); 6.35 (s, 2H, NH₂);
7.31–7.55 (m, 8H, aromat.)

e)
N-Hydroxy-N-{1-[3-(2,4,6-trimethyl-phenylethynyl)-phenyl]-ethyl}-urea

Melting point: 147°–149° C.
$^1$H-NMR (DMSO-d₆): 1.43, 1.45 (d, 3H, NCCH₃);
2.26 (s, 3H, CH₃);
2.42 (s, 6H, CH₃); 5.28–5.36 (m, 1H, NCH);
6.35 (s, 2H, NH₂); 6.94 (s, 2H, aromat.);
7.31–7.42 (m, 3H, aromat.); 7.49
(s, 1H, aromat.)

f)
N-Hydroxy-N-[3-(4-fluorophenylethynyl)-benzyl]-urea

Melting point: 166°–168° C.
$^1$H-NMR (DMSO-d₆): 4.55 (s, 2H, NCH₂); 6.42 (s, 2H, NH₂);
7.22–7.47 (m, 6H, aromat.);
7.59–7.64 (m, 2H, aromat.)

g)
N-Hydroxy-N-[3-(4-fluoro-naphth-1-yl-ethynyl)-benzyl]-urea

Melting point: 168°–170° C.
$^1$H-NMR (DMSO-d₆): 4.61 (s, 2H, NCH₂); 6.47 (s, 2H, NH₂);
7.37–7.47 (m, 3H, aromat.);
7.58–7.63 (m, 2H, aromat.); 7.72–7.86
(m, 3H, aromat.); 8.13, 8.16 (d, 1H, aromat.);
8.40, 8.43 (d, 1H, aromat.)

h)
N-Hydroxy-N-{1-[3-(3,4-dichlorophenylethynyl)-phenyl-]-ethyl}-urea

Melting point: 151°–152° C.
$^1$H-NMR (DMSO-d₆): 1.43, 1.45 (d, 3H, NCCH₃),
5.29–5.36
(m, 1H, NCH); 6.35 (s, 2H, NH₂);
7.34–7.45 (m, 3H, aromat.); 7.52–7.56
(m, 2H, aromat.); 7.65, 7.68 (d, 1H, aromat.);
7.83, 7.84 (d, 1H, aromat.)

EXAMPLE 9

N-Hydroxy-N-{1-[3-(4-methoxy-phenylethynyl)-phenyl]-ethyl}-urea 1.0 g 3-(4-methoxyphenyl-ethynyl)-acetophenone oxime (obtained in a manner analogous to that described in Examples 4a and 4b) dissolved in ml of glacial acetic acid was reduced using 0.355 g of sodium cyanoborohydride in the manner described in Example 1c. The hydroxylamine compound thus obtained was dissolved in 10 ml of absolute tetrahydrofuran and then 0.82 ml of trimethylsilylisocyanate were added dropwise. When the reaction was completed the mixture was diluted with ethyl acetate, mixed with a saturated solution of ammonium chloride, the organic layer was separated and washed with water. The crude product obtained after evaporation was stirred with ethyl acetate and filtered to give white crystals of the title compound melting at 141°–142° C. Yield: 0.851 g (72.8% of the theoretical).

$^1$H-NMR (DMSO-d₆): 1.41, 1.43 (d, 3H, NCCH₃);
3.79 (s, 3H, OCH₃);
5.27–5.34 (m, 1H, NCH); 6.34 (s, 2H, NH₂);
6.95–6.98 (m, 2H, aromat.); 7.29–7.37
(m, 2H, aromat.); 7.38–7.39 (m, 2H, aromat.);
7.47–7.50 (m, 2H, aromat.)

EXAMPLE 10

The procedure was the same as in Example 9 except there were used the appropriate reactants to give:

a)
N-Hydroxy-N-{1-[4-(3,4-dimethoxy-phenylethynyl)-phenyl]-ethyl}-urea

Melting point: 167° C.
$^1$H-NMR (DMSO-d₆): 1.40, 1.42 (d, 3H, NCCH₃);
3.79 (s, 3H, OCH₃);
3.80 (s, 3H, OCH ); 5.28–5.32 (m, 1H, NCH);
6.33 (s, 2H, NH₂); 6.96–6.99 (m, 1H, aromat.);
7.07–7.12 (m, 2H, aromat.); 7.34–7.37
(m, 2H, aromat.); 7.37–7.46 (m, 2H, aromat.)

b)
N-Hydroxy-N-{1-[3-(3,4-dimethoxy-phenylethynyl)-phenyl]-ethyl}-urea

Melting point: 144°–146° C.
$^1$H-NMR (DMSO-d₆): 1.41, 1.44 (d, 3H, NCCH₃);
3.79 (s, 3H, OCH₃);
3.80 (s, 3H, OCH₃); 5.27–5.32 (m, 1H, NCH);
6.33 (s, 2H, NH₂); 6.96–6.98 (m, 1H, aromat.);
7.10–7.14 (m, 2H, aromat.); 7.32–7.36
(m, 3H, aromat.); 7.48 (s, 1H, aromat.)

c)
N-Hydroxy-N-{1-[3-(3-methoxy-phenylethynyl)-phenyl]-ethyl}-urea

Melting point: 128°-130° C.
$^1$H-NMR (DMSO-d$_6$): 1.42, 1.44 (d, 3H, NCCH$_3$); 3.79 (s, 3H, OCH$_3$);
5.30-5.34 (m, 1H, NCH); 6.34 (s, 2H, NH$_2$); 6.96-7.10 (m, 1H, aromat.); 7.11-7.13 (m, 2H, aromat.); 7.30-7.42 (m, 4H, aromat.); 7.51 (s, 1H, aromat.)

d)
N-Hydroxy-N-{1-[3-(4-chloro-phenylethynyl)-phenyl]-ethyl}-urea

Melting point: 148°-149° C.
$^1$H-NMR (CDCl$_3$): 1.42, 1.43 (d, 3H, NCCH$_3$); 5.28-5.34
(m, 1H, NCH); 6.34 (s, 2H, NH$_2$); 7.32-7.59 (m, 8H, aromat.)

e)
N-Hydroxy-N-)3-(4-isopropyl-phenylethynyll-benzyl]-urea

Melting point: 148°-149° C.
$^1$H-NMR (DMSO-d$_6$): 1.20, 1.24 (d, 6H, C(CH$_3$)2); 2.87-2.96
(m, 1H, CH(C)$_2$); 4.55 (s, 2H, NCH$_2$); 6.39 (s, 2H, NH$_2$); 7.27-7.48 (m, 8H, aromat.)

f)
N-Hydroxy-N-{1-[3-(6-methoxy-naphth-2-yl-ethynyl)-phenyl]-ethyl}-urea

Melting point: 150°-152° C.
1H-NMR (DMSO-d$_6$): 1.43, 1.45 (d, 3H, NCCH$_3$); 3.89 (s, 3H, OCH$_3$);
5.29-5.36 (m, 1H, NCH); 6.35 (s, 2H, NH$_2$); 7.19-7.23 (m, 1H, aromat.); 7.35-7.57 (m, 6H, aromat.); 7.82-7.87 (m, 2H, aromat.); 8.10-8.17 (m, 1H, aromat.)

g)
N-Hydroxy-N-{1-[3-(2-methoxy-phenylethynyl)-phenyl]-ethyl}-urea viscous material $^1$H-NMR (DMSO-d$_6$): 1.42, 1.44 (d, 3H, NccH$_3$); 3.86 (s,3H, OCH$_3$);
5.27-5.34 (m, 1H, NCH); 6.34 (s, 2H, NH$_2$); 6.94-6.99 (m, 1H, aromat.); 7.06-7.09 (m, 1H, aromat.); 7.30-7.41 (m, 4H, aromat.); 7.46-7.49 (m, 2H, aromat.)

h)
N-Hydroxy-N-{1-[4-(4-methoxy-naphth-1-yl-ethynyl)-phenyl]-ethyl}-urea

Melting point: 153°-154° C.
$^1$H-NMR (DMSO-d$_6$): 1.43, 1.45 (d, 3H, NCCH$_3$); 4.02 (s, 3H, OCH$_3$);
5.31-5.38 (m, 1H, NCH); 6.35 (s, 2H, NH$_2$); 7.01, 7.04 (d, 1H, aromat.); 7.40-7.43 (m, 2H, aromat.); 7.57-7.77 (m, 5H, aromat.); 8.21, 8.24 (d, 1H, aromat.); 8.29, 8.32 (d, 1H, aromat.)

i)
N-Hydroxy-N-{1-[3-(4-methyl-phenylethynyl)-phenyl]-ethyl}-urea

Melting point: 142°-143° C.
$^1$H-NMR (DMSO-d$_6$): 1.42, 1.44 (d, 3H, NCCH$_3$); 2.35 (s, 3H, CH$_3$);
5.26-5.35 (m, 1H, NCH); 6.35 (s, 2H, NH$_2$); 7.22, 7.25 (d, 2H, aromat.); 7.31-7.50 (m, 6H, aromat.)

k)
N-Hydroxy-N-{1-[3-(2-methoxy-naphth-1-yl-ethynyl)-phenyl]-ethyl}-urea viscous material $^1$ H-NMR (DMSO-d$_6$): 1.44, 1.46 (d, 3H, NCCH$_3$); 4.02 (s, 3H, OCH$_3$);
5.30-5.37 (m, 1H, NCH); 6.38 (s, 2H, NH$_2$); 7.38-7.65 (m, 7H, aromat.); 7.92, 7.95 (d, 1H, aromat.); 8.00, 8.03 (d, 1H, aromat.); 8.21, 8.23 (d, 1H, aromat.)

l)
N-Hydroxy-N-[3-(2-methoxyphenylethynyl)-benzyl]-urea

Melting point: 122°-123.5° C.
$^1$H-NMR (DMSO-d$_6$): 3.86 (s, 3H, OCH$_3$); 4.54 (s, 2H, CH$_2$);
6.40 (s, 2H, NH$_2$); 6.94-6.99 (t, 1H, aromat.); 7.06, 7.09 (d, 1H, aromat.); 7.29-7.49 (m, 6H, aromat.)

m)
N-Hydroxy-N-[3-(4-chlorophenylethynyl)-benzyl]-urea

Melting point: 165°-166° C.
$^1$H-NMR (DMSO-d$_6$): 4.54 (s, 2H, NCH$_2$); 6.41 (s, 2H, NH$_2$);
7.35-7.59 (m, 8H, aromat.)

n)
N-Hydroxy-N-[3-(4-methoxyphenylethynyl)-benzyl]-urea

Melting point: 170° C.
$^1$H-NMR (DMSO-d$_6$): 3.79 (s, 3H, OCH$_3$); 4.54 (s, 2H, NCH$_2$);
6.40 (s, 2H, NH$_2$); 6.95-6.99 (m, 2H, aromat.); 7 28-7.50 (m, 6H; aromat.)

o)
N-Hydroxy-N-{1-[3-(3,4,5-trimethoxyphenylethynyl)-phenyl-1-ethyl}urea

Melting point: 166.5° C.
$^1$H-NMR (DMSO-d$_6$): 1.42, 1.44 (d, 3H, NCCH$_3$); 3.70 (s, 3H; OCH$_3$);
3.82 (s, 6H, OCH ); 5.28-5.30 (m, 1H, NCH); 6.33 (s, 2H, NH$_2$); 6.86 (s, 2H, aromat.); 7.31-7.41 (m, 3H, aromat.); 7.51 (s, 1H, aromat.)

p)
N-Hydroxy-N-[1-[3-(phenylethynyl)-phenyl]-ethyl}-urea

Melting point: 136°-137° C.
$^1$H-NMR (DMSO-d$_6$): 1.42, 144 (d, 3H, NCCH$_3$); 5.28-5.35
(m, 1H, NCH); 6.34 (s, 2H; NH$_2$); 7.32-7.57 (m, 9H, aromat.)

q) N-Hydroxy-N-[4-(2,6-dichlorophenylethynyl)-benzyl]-urea

Melting point: 157° C.
$^1$H-NMR (DMSO-d$_6$): 4.57 (s, 2H, NCH$_2$); 6.41 (s, 2H, NH$_2$);
7.36-7.45 (m, 3H, aromat.); 7.53-7.60 (m, 4H, aromat.)

EXAMPLE 11

N-Hydroxy-N-{1-[3-(4-trifluoromethyl-phenylethynyl)-phenyl]-ethyl}-urea a) 3-Ethynyl-acetophenone

Following the procedure described in Example 1a 12.53 g of 3-bromoacetophenone were reacted with 11 ml of trimethylsilylacetylene in presence of 0.62 g of bis-(triphenylphosphine)-palladium(II) chloride and 0.05 g of copper(I) iodide at a temperature of 40° to 50° C. The 3-(trimethylsilylethynyl)-acetophenone was isolated by column chromatography with petroleum ether/ether (3:1) and then dissolved in 100 ml of methanol to which solution, while chilling with ice-water, then were added 65 ml of 1n sodium hydroxide solution. After stirring for one hour 250 ml of a saturated solution of ammonium chloride were added and the mixture was extracted three times with 150 ml of ether each time. The extracts were washed twice with a saturated solution of sodium chloride, dried over sodium sulfate and then evaporated. Thus 8.60 g (96.2% of the theoretical yield) of the title compound in form of a slightly yellowish solid melting at 53-54° C. were obtained.

$^1$H-NMR (CDCl$_3$): 2.61 (s, 3H, COCH$_3$); 3.14 (s, 1H≡CH);
7.42-7.47 (m, 1H, aromat.); 7.66-7.70
(m, 1H, aromat.); 7.92-7.96 (m, 1H, aromat.);
8.07-8.08 (m, 1H, aromat.)

b) 3-(4-Trifluoromethyl-phenylethynyl)-acetophenone

In the manner described in Example 1a 8.60 g of the product obtained in Example 11a were reacted with 9.8 ml of 4-bromo-(trifluoromethyl-benzene) in presence of 0.63 g of bis(triphenylphosphine)-palladium(II) chloride and of 0.03 g of copper(I)iodide. By chromatography with petroleum ether/ether (2:1) 14.81 g (86.2% of the theoretical yield) of the title compound were obtained in the form of colorless crystals melting at 72-73° C.

$^1$H-NMR (CDCl$_3$): 2.64 (s, 3H, COCH$_3$); 7.46-7.52 (m, 1H, aromat.);
7.61-7.67 (m, 4H, aromat.); 7.72-7.75
(m, 1H, aromat.); 7.94-7.98 (m, 1H, aromat.);
8.13-8.14 (m, 1H, aromat.)

c) 3-(4-Trifluoromethyl-phenylethynyl)-acetophenone oxime

By reacting in the manner described in Example 1b 12.1 g of the product obtained in Example 11b with 4.90 g of hydroxylamine hydrochloride and 4.55 g of sodium acetate 12.32 g (96.5% of the theoretical yield) of the title compound melting at 117°-119° C. were obtained.

$^1$H-NMR (DMSO-d$_6$): 2.19 (s, 3H, N═CCH$_3$); 7.45-7.50
(m, 1H, aromat.); 7.58-7.62 (m, 1H, aromat.);
7.73-7.85 (m, 6H, aromat.)

d) N-Hydroxy-N-{1-[3-(4-trifluoromethyl-phenylethynyl)-phenyl]-ethyl}-urea

In the manner described in Example 7 3.52 g of the product obtained in Example 11c were reduced with 1.20 g of sodium cyanoborohydride to the corresponding hydroxylamine which then was reacted with 3.2 ml of trimethylsilylisocyanate. There were obtained 2.74 g (67.8% of the theoretical yield) of the title compound in the form of white crystals melting at 151°-152° C.

$^1$H-NMR (DMSO-d$_6$): 1.42, 1.44 (d, 3H, NCCH$_3$); 5.27-5.37
(m, 1H, NCH); 7.38-7.56 (m, 4H, aromat.);
7.78 (s, 4H, aromat.)

EXAMPLE 12

N-{1-3-(4-Chloro-phenylethynyl)-phenyl]-ethyl}-acetohydroxamic acid a) N-Acetoxy-N-{1-[3-(4-chloro-phenylethynyl)-phenyl]-ethyl}-acetamide 1.0 g of 3-(4-chloro-phenylethynyl)-acetophenone oxime were dissolved in 20 ml of hot ethanol, then chilled to 0° C. Then were added dropwise 0.82 ml of borane-pyridine complex and ten minutes later slowly 1.24 ml of 6n hydrochloric acid. After stirring for two hours at 0° C. an additional amount of 3 ml of hydrochloric acid was slowly added. During the next two hours the temperature was allowed to warm to 15° C. and then the solution was stirred for additional two hours at 3° C. Sodium carbonate was added thereafter in small portions until the mixture showed p 8. After adding ether the organic layer was separated, washed three times with saturated sodium chloride solution, dried over sodium sulfate and evaporated in a vacuum to yield a slightly brownish oil. This was dissolved in 10 ml of anhydrous tetrahydrofuran and, while chilling in ice-water, 1.51 ml of pyridine followed by 1.32 ml of acetylchloride were added. (TLC: petroleum ether-/ethyl acetate—1:1). When the reaction was finished ethyl acetate and a saturated solution of sodium hydrogen carbonate were added, the organic layer was separated, washed with saturated sodium chloride soluscous oily residue was purified by chromatography with petroleum ether/ethyl acetate (1:1) to yield 1.039 g (83.5% of the theoretical yield) of the title compound as a colorless oil.

$^1$H-NMR (CDCl ): 1.53, 1.56 (d, 3H, NCCH$_3$); 2.13 (s, 3H, NOCOCH$_3$);
2.16 (s, 3H, NCOCH$_3$); 5.70-5.85 (m, 1H, NCH);
7.15-7.54 (m, 8H, aromat.)

b) N-{1-[3-(4-Chloro-phenylethynyl)-phenyl]-ethyl}-acetohydroxamic acid

The procedure was the same as described in Example 4d except there were used 1.031 g of the product obtained in Example 12a, 0.20 g of anhydrous-potassium carbonate and 11 ml of methanol. On chromatography of the raw product with petroleum ether/ethyl acetate (1:1) 0.786 g (89.2% of the theoretical yield) of the title compound were obtained in form of white crystals melting at 129° C.

$^1$H-NMR (DMSO-d$_6$): 1.46, 1.48 (d, 3H, NCCH$_3$); 2.02 (s, 3H, NCOCH$_3$);
5.53-5.68 (m, 1H, NCH); 7.27-7.56
(m, 6H, aromat.); 7.57-7.59 (m, 2H, aromat.)

EXAMPLE 13

Following the procedure described in Example 12 there were obtained from the appropriate reactants:

a) N-{1-[4-(4-Isopropyl-phenylethynyl)-phenyl]-ethyl}-acetohydroxamic acid

Colorless crystals melting at 142°-143° C.

$^1$H-NMR (DMSO-d$_6$): 1.20, 1.22 (d, 6H, C(CH$_3$)2); 1.45, 1.47 (d, 3H, NCCH ); 2.02 (s, 3H, NCOCH$_3$); 2.87-2.96 (m, 1H, CH(C) ); 5.57-5.71 (m, 1H, NCH); 7.20-7.36 (m, 4H, aromat.);

b)

N-[4-(2,6-Dichlorophenylethynyl)-benzyl]-acetohydroxamic acid

Melting point: 139°-139.5° C.
$^1$H-NMR (DMSO-d$_6$): 2.06 (s, 3H, NCOCH$_3$); 4.73 (s, 2H, NCH$_2$);
7.34-7.45 (m, 3H, aromat.); 7.55-7.60 (m, 4H, aromat.)

EXAMPLE 14

N-{1-[4-(Thien-2-yl-ethynyl)-phenyl]-ethyl}-acetohydroxamic acid a) 4-(Thien-2-yl -ethynyl)-acetophene Following the procedure described in Example 1a 4-bromoacetophenone and 2-thienylacetylene in triethylamine were reacted in presence of bis-(triphenylphosphine)-palladium(II) chloride and of copper(I) iodide to yield (after purification by chromatography with n-hexane/ethyl acetate—9:1) the title compound in form of a yellowish oil.

$^1$H-NMR (CDCl$_6$): 2.61 (s, 3H, COCH$_3$); 7.05 (dd, 1H, aromat.);
7.34 (m, 2H, aromat.); 7.59 (m, 2H, aromat.); 7.93 (m, 2H, aromat.)

b) 4-(Thien-2-yl -ethynyl)-acetophenone oxime 4.03 g of hydroxylamine hydrochloride, 6.57 g of the product obtained in Example 14a and 3.07 g of sodium carbonate were reacted in 150 ml of a mixture of ethanol and water (2:1) at room temperature. The raw product was recrystallized from ethyl acetate to yield 4.62 g (66.0% of the theoretical yield) of the colorless title compound. Melting point 187°-188° C.

$^1$H-NMR (CDCl$_3$): 2.25 (s, 3H, N=CCH$_3$); 7.03 (dd, 1H, aromat.);
7.31 (m, 2H, aromat.); 7.48 (m, 2H, aromat.); 7.66 (m, 2H, aromat.)

c)

N-{1-[4-(Thien-2-yl-ethynyl)-phenyl]-ethyl}-hydroxylamine i) To a solution of 0.24 g of the product of Example 14b in 5 ml of glacial acetic acid at room temperature were added 0.252 g of sodium cyanoborohydride and after stirring for 30 minutes additional 0.126 g of sodium cyanoborohydride followed by stirring for further 30 minutes. The reaction mixture was used as starting material in Example 14d.

ii) To a solution of 0.24 g of the product obtained in Example 14b and of 0.125 g of sodium cyanoborohydride in 5 ml of ethanol were added three drops of a saturated ethanolic solution of methyl orange. To this mixture, while stirring at room temperature, were slowly added 1.05 ml of a 10% solution of hydrogen chloride in ethanol until the pink colour maintained for 30 seconds. The reaction mixture was poured into 30 ml of saturated sodium chloride solution and then extracted three times with 15 ml of ethyl acetate each time. The extracts were washed with 10 ml of saturated sodium hydrogen carbonate solution, dried over magnesium sulfate and evaporated in a vacuum. The raw product was purified by chromatography with n-hexane/isopropanol (9:1) to yield 0.088 g (36% of the theoretical yield) of the title compound in form of a yellowish oil.

iii) To a solution of 0.24 g of the product obtained in Example 14b were added at 0° C. in an atmosphere of nitrogen 0.2 ml of borane-pyridine complex. After stirring for 15 minutes 1.6 ml of a 20% solution of hydrogen chloride in ethanol were added. The mixture was stirred for one hour at room temperature and then poured into 30 ml of saturated sodium chloride solution. By adding potassium carbonate the p$_H$ was adjusted to 9. The mixture was extracted three times with 10 ml of ethyl acetate each time, the organic extracts were dried over magnesium sulfate and evaporated in a vacuum. Thus 0.25 g (practically quantitative yield) of the product were obtained as a yellowish oil.

d)

N-Acetoxy-N-{1-[4-(thien-2-yl-ethynyl)-phenyl]-ethyl}-acetamide i) To the reaction mixture obtained in Example 14c)i) were added 0.5 ml of acetic anhydride and after stirring for 16 hours this mixture was poured in small portions to a solution of 7.0 g of sodium hydrogen carbonate in 100 ml of water. When the formation of carbon dioxide came to an end the mixture was extracted three times with 30 ml of ethyl acetate each time. The extracts were dried over magnesium sulfate, evaporated in a vacuum and the residue was purified by chromatography with n-hexane/ethyl acetate (4:1). Thus 0.16 g (49% of the theoretical yield calculated on the amount of starting material used in Example 14c)i) of a yellowish oil were obtained.

$^1$H-NMR (CDCl$_3$): 1.46 (d, 3H, NCCH ); 1.98 (s, 3H, NCOCH$_3$);
2.18 (s, 3H, OCOCH$_3$); 5.67 (m, 1H, NCH);
7.13 (dd, 1H, aromat.); 7.41 (m, 3H, aromat.);
7.52 (d, 2H, aromat.); 7.65 (m, 1H, aromat.)

ii) To a solution of 0.25 g of the product obtained in Example 14c)iii) in 5 ml of toluene were added 1 ml of acetic anhydride and 0.2 ml of pyridine. The mixture was boiled under reflux for 2 hours, cooled to room temperature and then poured into a mixture of 25 ml of saturated sodium chloride solution and 2 ml of 1n hydrochloric acid. The organic layer was separated, the aqueous layer was extracted twice with 15 ml of ethyl acetate each time. The combined organic extracts were washed with 5 ml of saturated sodium chloride solution, dried over magnesium sulfate and evaporated in a vacuum. The remaining oil was chromatographed with n-hexane/isopropanol (9:1) to yield 0.20 g (61% of the theoretical yield) of a yellowish oil.

e)

N-{1-[4-(Thien-2-yl-ethynyl)-phenyl]-ethyl}-acetohydroxamic acid

At room temperature to a solution of 0.145 g of the product obtained in Example 14d were added 0.57 ml of a 1-molar solution of lithium hydroxide in methanol and after stirring for 30 minutes the mixture was poured to 4 ml of saturated sodium chloride solution and 1 ml of saturated sodium hydrogen carbonate solution. The mixture was extracted three times with 2 ml of ethyl acetate each time, the organic extracts were washed with 1 ml of saturated sodium chloride solution, dried over magnesium sulfate and evaporated in a vacuum. The crude product was recrystallized from n-hexane/ethyl acetate to yield 0.065 g (52% of the theoretical yield) of the title compound as a colorless solid.
Melting point: 128°–129° C.
¹H-NMR (DMSO-d₆): 1.46 (d, 3H, NCCH₃); 2.03 (s, 3H, NCOCH₃);
5.63 (m, 1H, NCH); 7.11 (dd, 1H, aromat.);
7.37 (m, 3H, aromat.); 7.49 (d, 2H, aromat.);
7.64 (m, 1H, aromat.)

EXAMPLE 15

N-Hydroxy-N-{1-[4-(thien-2-yl-ethynyl)-phenyl]-ethyl}-urea 1.37 g of the hydroxylamine derivative prepared in Example 14c), dissolved in 25 ml of tetrahydrofuran, were reacted with 1 ml of trimethylsilylisocyanate in a manner as described in Example 7. The reaction mixture was worked up as usual and the crude product was recrystallized from n-hexane/ethylacetate. 0.662 g (46.0% of the theoretical yield) of the title compound were obtained in form of a colorless solid melting at 154°–155° C.
¹H-NMR (DMSO-d₆): 1.53 (d, 3H, NCCH₃); 5.48 (q, 1H, NCH);
5.59 (s, 2H, NH₂); 7.02 (dd, 1H, aromat.);
7.29 (m, 2H, aromat.); 7.44 (m, 4H, aromat.)

EXAMPLE 16

By using the appropriate reactants and otherwise proceeding as described in Examples 14 and 15 there were obtained:

a)
N-{1-[4-(Thien-3-yl-ethynyl)-phenyl]-ethyl}-acetohydroxamic acid

Melting point: 130°–131° C.
¹H-NMR (DMSO-d₆): 1.51 (d, 3H, NCCH₃); 2.09 (s, 3H, NCOCH₃);
5.69 (m, 1H, NCH); 7.33 (dd, 1H, aromat.);
7.41 (m, 2H, aromat.); 7.56 (m, 2H, aromat.);
7.70 (dd, 1H, aromat.); 7.95 (dd, 1H, aromat.)

b)
N-Hydroxy-N-{1-[4-(thien-3-yl-ethynyl)-phenyl]-ethyl}-urea

Melting point: 156°–157° C.
¹H-NMR (DMSO-d₆): 1.42 (d, 3H, NCCH₃); 5.32 (q, 1H, NCH);
6.33 (s, 2H, NH₂); 7.24 (dd, 1H, aromat.);
7.37 (d, 2H, aromat.); 7.45 (d, 2H, aromat.);
7.62 (dd, 1H, aromat.); 7.84 (dd, 1H, aromat.)

c) N-[4-(Thien-2-yl-ethynyl)-benzyl]-acetohydroxamic acid

Melting point: 113°–114° C.
¹H-NMR (DMSO-d₆): 2.06 (s, 3H, NCOCH₃); 4.71 (s, 2H, NCH₂);
7.12 (dd, 1H, aromat.); 7.31 (d, 2H, aromat.);
7.40 (dd, 1H, aromat.); 7.51 (d, 2H, aromat.);
7.64 (dd, 1H, aromat.)

d) N-Hydroxy-N-[4-(thien-2-yl-ethynyl)-benzyl]-urea 7.11 (m, 1H, aromat.); 7.34 (d, 2H, aromat.);
7.40 (d, 1H, aromat.); 7.49 (d, 2H, aromat.);
7.63 (d, 1H, aromat.)

e) N-[4-(Thien-3-yl-ethynyl)-benzyl]-acetohydroxamic acid

Melting point: 147°–152° C.
¹H-NMR (DMSO-d₆): 2.06 (s, 3H, NCOCH₃); 4.71 (s, 2H, NCH₂);
7.25 (d, 1H, aromat.); 7.30 (d, 2H, aromat.);
7.49 (d, 2H, aromat.); 7.63 (m, 1H, aromat.);
7.86 (d, 1H, aromat.)

f) N-Hydroxy-N-[4-(thien-3-yl-ethynyl)-benzyl]-urea

Melting point: 187°–188° C. (decomp.)
¹H-NMR (DMSO-d₆): 4.56 (s, 2H, NCH₂); 6.41 (s, 2H, NH₂);
7.25 (d, 1H, aromat.); 7.33 (d, 2H, aromat.);
7.47 (d, 2H, aromat.); 7.62 (m, 1H, aromat.);
7.85 (m, 1H, aromat.)

g)
N-Hydroxy-N-{1-[4-(5-chloro-thien-2-yl-ethynyl)-phenyl]-ethyl}urea

Melting point: 151°–152° C.
¹H-NMR (DMSO-d₆): 1.42 (d, 3H, NCCH₃); 5.34 (q, 1H, NCH);
6.36 (s, 2H, NH₂); 7.13 (d, 1H, aromat.);
7.28 (d, 1H, aromat.); 7.39 (d, 2H, aromat.);
7.47 (d, 2H, aromat.)

h)
N-{1-[4-(5-Chloro-thien-2-yl-ethynyl)-phenyl]-ethyl}-acetohydroxamic acid Melting point: 130°–131° C.
¹H-NMR (DMSO-d₆): 1.47 (d, 3H, NCCH₃); 2.04 (s, 3H, NCOCH₃);
5.64 (m, 1H, NCH); 7.13 (d, 1H, aromat.);
7.28 (d, 1H, aromat.); 7.37 (d, 2H, aromat.);
7.50 (d, 2H, aromat.)

i)
N-Hydroxy-N-{1-[4-(benzothien-2-yl-ethynyl)-phenyl]-ethyl}-urea

Melting point: 164°–165° C.
¹H-NMR (DMSO-d₆): 1.44 (d, 3H, NCCH₃); 5.35 (m, 1H, NCH);
6.37 (s, 2H, NH₂); 7.35–7.96 (m, 9H, aromat.)

k)
N-{1-[4-(Benzothien-2-yl-ethynyl)-phenyl]-ethyl}-acetohydroxamic acid

Melting point: 172°–173° C.
¹H-NMR (DMSO-d₆): 1.49 (d, 3H, NCCH₃); 2.06 (s, 3H, NCOCH₃);
5.67 (m, 1H, NCH); 7.39–7.45 (m, 4H, aromat.);
7.56 (d, 2H, aromat.); 7.74 (s, 1H, aromat.);
7.86 (m, 1H, aromat.); 7.95 (m, 1H, aromat.)

EXAMPLE 17

The procedure was the same as described in Example 12 there were used, however, as starting materials the respective (pyridine-3-yl-ethynyl)acetophenone or -benzaldehyde oximes to prepare:

a)
N-{1-[4-(Pyridin-3-yl-ethynyl)-phenyl]-ethyl}-acetohydroxamic acid

Melting point: 121° C.
¹H-NMR (DMSO-d₆): 1.45, 1.48 (d, 3H, NCCH₃); 2.03 (s, 3H, NCOCH₃);
5.63–5.65 (m, 1H, NCH); 7.37–7.56 (m, 5H, aromat.); 7.94–7.99 (m, 1H, aromat.);
8.57–8.59 (m, 1H, aromat.); 8.73, 8.74 (d, 1H, aromat.)

b) N-[4-(Pyridin-3-yl-ethynyl)-benzyl]-acetohydroxamic acid

Melting point: 125.5° C.
$^1$H-NMR (DMSO-d$_6$): 2.06 (s, 3H, NCOCH$_3$); 4.72 (s, 2H, NCH$_2$);
7.31–7.34 (m, 2H, aromat.); 7.45–7.47 (m, 1H, aromat.); 7.54–7.57 (m, 2H, aromat.); 7.95–7.97 (m, 1H, aromat.); 8.57–8.59 (m, 1H, aromat.); 8.74, 8.75 (d, 1H, aromat.)

c) N-3-(Pyridin-3-yl-ethynyl)-benzyl -acetohydroxamic acid

Melting point: 114.5°–115.5° C.
$^1$H-NMR (DMSO-d$_6$) 2.07 (s, 3H, NCOCH$_3$); 4.71 (s, 2H, NCH$_2$);
7.33–7.51 (m, 5H, aromat.); 7.97–7.99 (m, 1H, aromat.); 8.58–8.60 (m, 1H, aromat.); 8.76, 8.77 (d, 1H, aromat.)

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations falling within the scope of the appended claims and equivalents thereof.

What we claim is:

1. A substituted phenylacetylene of the formula

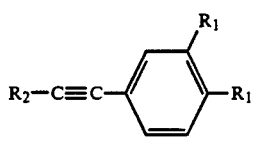   I wherein
one of the symbols R$_1$ represents a hydrogen atom while the other represents the group of the formula

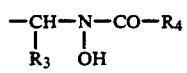

in which
R$_3$ is hydrogen, methyl or ethyl and R$_4$ represents a methyl or an amino group and
R$_2$ represents a mono- or binuclear group which is a mono- or binuclear heterocyclic radical containing sulfur nitrogen or oxygen selected from the group consisting of radicals of the formulae

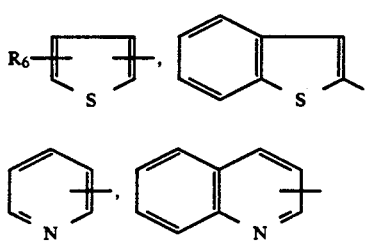

and

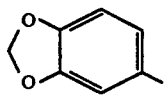

wherein R$_6$ represents a hydrogen or a chlorine atom or a methyl group
or a stereoisomer or optically active form thereof.

2. A substituted phenylacetylene according to claim 1, wherein R$_1$ and R$_4$ have the same meanings as defined in claim 1, R$_3$ represents a hydrogen atom or a methyl group, and R$_2$ represents a mono- or binuclear radical which is a mono- or binuclear heterocyclic radical containing sulfur or oxygen selected from the group consisting of radicals of the formualae

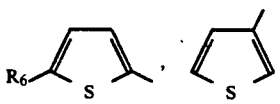

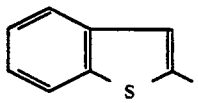

and

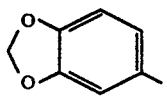

wherein R$_6$ represents a hydrogen or a chlorine atom or a methyl group or a stereoisomer or optically active form thereof.

3. A substituted phenylacetylene according to claim 2, wherein R$_2$ represents one of the groups

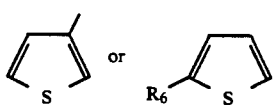

in which R$_6$ has the meaning defined in claim 2.

4. A substituted phenylacetylene according to claim 1, wherein R$_2$ represents a quinolyl-3 group or a pyridyl-3 group.

5. A substituted phenylacetylene according to claim 2, wherein R$_6$ represents a hydrogen atom.

6. A substituted phenylacetylene according to claim 1, corresponding to the formula

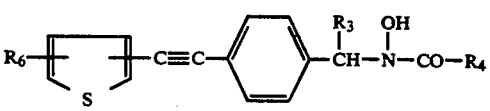

wherein R$_3$, R$_4$ and R$_6$ have the same meanings given in claim 1.

7. A substituted phenylacetylene according to claim 2, corresponding to the formula

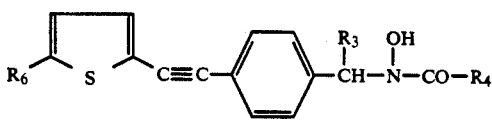

wherein $R_3$ represents a hydrogen atom or a methyl group, $R_4$ represents a methyl or an amino group, and $R_6$ has the same meaning given in claim 2.

8. A substituted phenylacetylene according to claim 2, corresponding to the formula

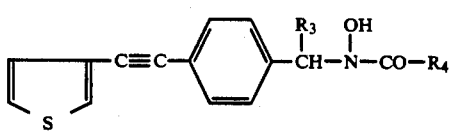

wherein $R_3$ represents a hydrogen atom or a methyl group $R_4$ represents a methyl or an amino group.

9. A pharmaceutical composition for parenteral, oral, intranasal, rectal or percutaneous application comprising an effective 5-lipoxygenase inhibiting amount of at least one substituted phenylacetylene according to claim 1 and a pharmaceutically acceptable carrier or diluent.

10. A pharmaceutical composition according to claim 9, comprising from about 0.01 to 50 mg of said substituted phenylacetylene per individual dose.

11. A pharmaceutical composition according to claim 10, suitable for parenteral or oral administration and containing from about 0.01 to 10 mg of said substituted phenylacetylene per individual dose.

12. A pharmaceutical composition according to claim 10, for oral administration in the form of tablets, coated tablets or capsules.

13. A pharmaceutical composition according to claim 12, wherein the substituted phenylacetylene is in delayed release form.

14. A pharmaceutical composition according to claim 9, suitable for intranasal or oral application or for administration of the active ingredient to the bronchia in spray form containing said substituted phenylacetylene dissolved in a pharmaceutically acceptable liquid carrier.

15. A pharmaceutical composition according to claim 9, suitable for percutaneous application comprising a reservoir attachable to the skin of the patient and containing said substituted phenylacetylene dissolved in a liquid carrier.

16. A pharmaceutical composition according to claim 15, wherein said liquid carrier includes a membrane penetration enhancing agent.

* * * * *